United States Patent
Ro et al.

(12)

(10) Patent No.: US 6,340,748 B1
(45) Date of Patent: Jan. 22, 2002

(54) PROMOTER OF THE TOMATO EXPANSIN GENE LEEXP-1

(76) Inventors: Seungil Ro, 3300 Kauai Ct., E7, Reno, NV (US) 89509; Nicholas Ewing, 1637 La Paloma Ct., Davis, CA (US) 95616

( * ) Notice: Subject to any disclaimer, the term of this patent is extended or adjusted under 35 U.S.C. 154(b) by 0 days.

(21) Appl. No.: 09/671,545

(22) Filed: Sep. 27, 2000

Related U.S. Application Data

(60) Provisional application No. 60/156,494, filed on Sep. 28, 1999.

(51) Int. Cl.[7] .................................................. C07H 21/04
(52) U.S. Cl. ....................................... 536/24.1; 536/23.1
(58) Field of Search ............................... 435/320.1, 410, 435/468; 800/295, 278, 285, 286, 287, 298; 536/23.1, 24.1

(56) References Cited

PUBLICATIONS

Rose, J. et al., 1997, Proc Natl. Acad. Sci. USA, vol. 94 (11), p. 5955–5960.*
Brummel, D. et al., 1999, Plant Mol. Biol., vol. 39 (1), p. 161–169.*

* cited by examiner

*Primary Examiner*—David Guzo
*Assistant Examiner*—Lauren Nguyen
(74) *Attorney, Agent, or Firm*—James M. Ritchey

(57) ABSTRACT

A tomato promoter (LeExp-1 shown in SEQ ID NO: 1) was isolated which can direct a high level of fruit-specific expression. This promoter can be fused to any DNA sequence (including, but not limited to, plant, animal, fungal, algal, and bacterial genes that encode proteins as well as DNA sequences that produce biologically active RNAs following transcription, including antisense RNAs and ribozymes) to direct a high level of transcription in tomato fruit.

1 Claim, 2 Drawing Sheets

-566 GATCATAGGCTCTGCATCGGTATTATAGAGTGATCTCCATGCCTTTGTTTCTTTGTGAAG

-506 ATTCTGGTGGAAATTGATAGTCTCCTTTGATCTCTAAGGGTTCATCTAAGGTAGTTTCTT

-446 TACTAACCAACCTATCAATGTTATTAAACCTTCTATGACAGTTTACAGTCCTATGAAATG
      SP8b
-386 ATTTGGTGTTTTTGTCCCCTTCTTTAAGCCACCAACTTTCGAATGAGCATTGCAGTATGC
                  AuxRE
-326 GATTCATATTTAGTTGAACCTCAAATGCGAGTGAAATTTGAAAATAC<u>AAACACA</u>ACGCAT

-266 CT<u>AAACACAC</u>ATTTAAGACATCTAAAATCAATGGACTGTACCAACCTATTATGTCAATAG
                                       SP8a              AuxRE
-206 TGTTCAAAATATGTTATTTAATCACTTTGTATATTCAATATTTTTTCCGACGATTGGAC
                                    2
-146 ACCTAAAAATAAGACAAAACAAAAAACATAATAAATATTATTTCTTTTTATGTTTTTGTT

-86  CCCGCCAATATGGTCCTTTGATTAAGGAGGACCAAACTTAAGTATTCACACATAATTTCT
          1                    +1           *
-26  CTGGTATAAGTAGTGCTTCTCGTTGCATCATTTTCTTCAACAACTTCAATTCCATTAAAT
         2                 ↑ Predicted Transcriptional start site
+35  CTTAAGAATGGGTATCATAATTTTCATCCTTGTTCTTCTTTTTGTAGACTCATGTTTC
            M  G  I  I  I  F  I  L  V  L  L  F  V  D  S  C  F

FIGURE 1

-566 GATCATAGGCTCTGCATCGGTATTATAGAGTGATCTCCATGCCTTTGTTTCTTTGTGAAG

-506 ATTCTGGTGGAAATTGATAGTCTCCTTTGATCTCTAAGGGTTCATCTAAGGTAGTTTCTT

-446 TACTAACCAACCTATCAATGTTATTAAACCTTCTATGACAGTTTACAGTCCTATGAAATG

-386 ATTTGGTGTTTTTGTCCCCTTCTTTAAGCCACCAACTTTCGAATGAGCATTGCAGTATGC

-326 GATTCATATTTAGTTGAACCTCAAATGCGAGTGAAATTTGAAAATACAAACACAACGCAT

-266 CTAAACACACATTTAAGACATCTAAAATCAATGGACTGTACCAACCTATTATGTCAATAG

-206 TGTTCAAAATATGTTATTTAATCACTTTGTATATTCAATATTTTTTCCGACGATTGGAC

-146 ACCTAAAAATAAGACAAAACAAAAAACATAATAAATATTATTTCTTTTTATGTTTTTGTT

-86 CCCGCCAATATGGTCCTTTGATTAAGGAGGACCAAACTTAAGTATTCACACATAATTTCT

-26 CTGGTATAAGTAGTGCTTCTCGTTGCATCATTTTCTTCAAC

SEQUENCE LISTING

<160> NUMBER OF SEQ ID NOS: 6

<210> SEQ ID NO 1
<211> LENGTH: 581
<212> TYPE: DNA
<213> ORGANISM: Lycopersicon esculentum

<400> SEQUENCE: 1

```
gatcataggc tctgcatcgg tattatagag tgatctccat gcctttgttt ctttgtgaag     60
attctggtgg aaattgatag tctcctttga tctctaaggg ttcatctaag gtagtttctt    120
tactaaccaa cctatcaatg ttattaaacc ttctatgaca gtttacagtc ctatgaaatg    180
atttggtgtt tttgtcccct tctttaagcc accaactttc gaatgagcat tgcagtatgc    240
gattcatatt tagttgaacc tcaaatgcga gtgaaatttg aaaatacaaa cacaacgcat    300
ctaaacacac atttaagaca tctaaaatca atggactgta ccaacctatt atgtcaatag    360
tgttcaaaat atgttattta atcactttgt atattcaata ttttttttccg acgattggac    420
acctaaaaat aagacaaaac aaaaaacata ataaatatta tttcttttta tgtttttgtt    480
cccgccaata tggtcctttg attaaggagg accaaactta agtattcaca cataatttct    540
ctggtataag tagtgcttct cgttgcatca ttttcttcaa c                        581
```

<210> SEQ ID NO 2
<211> LENGTH: 658
<212> TYPE: DNA
<213> ORGANISM: Lycopersicon esculentum

<400> SEQUENCE: 2

```
gatcataggc tctgcatcgg tattatagag tgatctccat gcctttgttt ctttgtgaag     60
attctggtgg aaattgatag tctcctttga tctctaaggg ttcatctaag gtagtttctt    120
tactaaccaa cctatcaatg ttattaaacc ttctatgaca gtttacagtc ctatgaaatg    180
atttggtgtt tttgtcccct tctttaagcc accaactttc gaatgagcat tgcagtatgc    240
gattcatatt tagttgaacc tcaaatgcga gtgaaatttg aaaatacaaa cacaacgcat    300
ctaaacacac atttaagaca tctaaaatca atggactgta ccaacctatt atgtcaatag    360
tgttcaaaat atgttattta atcactttgt atattcaata ttttttttccg acgattggac    420
acctaaaaat aagacaaaac aaaaaacata ataaatatta tttcttttta tgtttttgtt    480
cccgccaata tggtcctttg attaaggagg accaaactta agtattcaca cataatttct    540
ctggtataag tagtgcttct cgttgcatca ttttcttcaa caacttcaat tccattaaat    600
cttaagaatg ggtatcataa ttttcatcct tgttcttctt tttgtagact catgtttc     658
```

<210> SEQ ID NO 3
<211> LENGTH: 23
<212> TYPE: DNA
<213> ORGANISM: Lycopersicon esculentum

<400> SEQUENCE: 3

```
ggaacaatgg gcggtgcgtg tgg                                            23
```

<210> SEQ ID NO 4
<211> LENGTH: 26
<212> TYPE: DNA
<213> ORGANISM: Lycopersicon esculentum

<400> SEQUENCE: 4

```
gcatgtgcag tttcccatga accacc                                         26
```

<210> SEQ ID NO 5
<211> LENGTH: 20
<212> TYPE: DNA
<213> ORGANISM: Lycopersicon esculentum
```

```
<400> SEQUENCE: 5
ttatacagcc aaggatacgg                                    20

<210> SEQ ID NO 6
<211> LENGTH: 21
<212> TYPE: DNA
<213> ORGANISM: Lycopersicon esculentum

<400> SEQUENCE: 6
gtaaacacca gggattcttc c                                  21
```

PROMOTER OF THE TOMATO EXPANSIN GENE LEEXP-1

Priority is claimed to Provisional Application No: 60/156,494 filed on Sep. 28, 1999.

BACKGROUND OF THE INVENTION

1. Field of the Invention

The promoter of the tomato expansin gene LeExp-1 was cloned. The cDNA sequence for the tomato expansin LeExp-1 (Rose, et al., 1997) was used to design primers used in a method called inverse PCR to PCR the region upstream of the known cDNA sequence. This technique was utilized successfully to obtain the region that includes 566 base pairs upstream of the likely transcriptional start site. Also, PCR was employed to clone the remainder of the gene. The subject invention comprises the 581 bp promoter sequence (See FIG. 2 and SEQ ID NO: 1).

2. Description of the Background Art

The subject promoter, LeExp-1, normally directs expression of the tomato expansin LeExp-1 as reported in Rose et al. (this and all references cited in this disclosure are incorporated herein by reference). These authors isolated a cDNA clone and reported its sequence. Applicants used this reported sequence as a starting point to isolate a genomic clone using a PCR based approach. It is respectfully submitted that this information does not teach or render obvious applicant's claimed invention.

SUMMARY OF THE INVENTION

An object of the present invention is to disclose a promoter used to direct the expression of any gene to a high level.

Another object of the present invention is to present a promoter used to direct the expression of any gene to a high level, specifically in tomato fruit which is an excellent, cost-effective, large-scale expression system.

A further object of the present invention is to disclose a vector or DNA construct including the subject DNA sequence disclosed herein.

Still another object of the present invention is to relate a dicotyledonous plant cell or protoplast transformed with the subject DNA sequence disclosed herein.

Yet a further object of the present invention is to describe a method for enhancing gene expression comprising transforming cells or protoplasts with the subject DNA sequence and a heterologous coding sequence operably joined to the regulatory region, selecting the cells or protoplasts which have been transformed, regenerating the selected and transformed cells or protoplasts, and selecting organisms which express the heterologous gene.

Disclosed is a tomato promoter, LeExp-1, which is included in FIG. 1 and, in particular, shown in FIG. 2 (also, see SEQ ID NO: 1). Among other attributes, the LeExp-1 promoter can direct a high level of fruit-specific expression. The LeExp-1 promoter can be fused to any DNA sequence (including, but not limited to, plant, animal, fungal, algal, and bacterial genes that encode proteins as well as DNA sequences that produce biologically active RNAs following transcription, including antisense RNAs and ribozymes) to direct a high level of transcription in tomato fruit.

More specifically, a primary subject goal was to isolate a promoter that could be utilized to drive a high level of expression of any gene in tomato fruit. To identify a promoter that would allow this the literature was examined for genes which had been shown to be expressed at high levels in tomato fruit and it was concluded that LeExp-1 is among the most highly expressed tomato fruit-specific genes identified to date (Rose et al., 1997). Since promoters are responsible for the control of gene expression the promoter of LeExp-1 was targeted for this invention since it would direct expression of any DNA sequence fused to it in the tomato fruit specific pattern observed for LeExp-1. The published LeExp-1 cDNA sequence represents a DNA copy of the LeExp-1 mRNA and so does not include the promoter for the LeExp-1 gene. Therefore, we set out to, and accomplished, the cloning of the LeExp-1 promoter. Prior to our cloning and DNA sequence analysis of the LeExp-1 promoter the sequence of the promoter of LeExp-1 was unknown.

In order to clone the promoter of the LeExp-1 gene we utilized a technique commonly referred to as inverse PCR® or IPCR (Ochman et al., 1993) which allows unknown regions of DNA to be cloned if an adjacent region is known. To accomplish this, we made use of the published sequence of the LeExp-1 cDNA (Rose, et al.,; Genbank Accession; U.S. Pat. No. :5,929,303).

The first step in the IPCR approach is to choose restriction enzymes that will cleave the genomic region of interest near the unknown region that is to be amplified by IPCR. To accomplish this for LeExp-1, the cDNA sequence was examined for restriction sites located near the 5' end of the cDNA sequence. Since the DNA sequence of the upstream region was not known, it could not be determined without further experiments where the selected restriction enzymes would cut upstream. For success, inverse PCR requires the chance occurrence of a second site no further than approximately 6 kb upstream. If no sites for the selected enzyme occur within this distance, the strategy will not be successful. To increase the likelihood that a second site would occur within 6 kb upstream, an additional strategy was attempted here in which a second enzyme that generated compatible termini was used in a double digestion with the enzymes known to cut the cDNA insert. In this case, BcLI and BamHI were used in a double digestion.

In the next step, the digested genomic DNA was circularized by ligation with T4 DNA ligase. Circularization brings the two positions in the known sequence into juxtaposition with the unknown 5' sequences. The known sequences then serve as oligonucleotide priming sites to amplify the 5' unknown sequence. Following the first round of amplification, two nested primers were used to direct a second round of amplification.

The first pair of oligonucleotide primers were designed for inverse PCR in such a way that they annealed to the target DNA template 29 bp apart, and their 3'-termini were oriented in opposite directions. The oligonucleotide primers were designated LeExp-1-7 (5'GGAACAATGGGCGGT-GCGTGTGG 3')SEQ ID NO:3 and LeExp-1-8 rev. (5'GCATGTGCAGTTTCCCATGAACCACC 3'), SEQ ID NO:4 corresponding to the nucleotide sequences at 169–191 bp and 115–140 bp of the LeExp-1 cDNA, respectively. The two nested primers, designated LeExp-1-2 and LeExp-1-3 rev., were 5' TTATACAGCCA AGGATACGG 3'(201–221) SEQ ID NO:5 and 5' GTAAACACCAGGGATTCTTCC 3'(111–91) SEQ ID NO:6.

Inverse PCR was carried out with the two divergent primers, LeExp-1-7 and LeExp-1-8rev in a standard PCR reaction. Since the first PCR products were not visible on an agarose gel (data not shown), a second round of PCR was performed with the two nested primers, designated LeExp-1-2 and LeExp-1-3rev. A 1.4 kb PCR product was obtained from 500 ng of BcLI and BamHI digested and circularized tomato genomic DNA and subcloned into the vector pCR1000 (InVitrogen, Inc).

This clone was designated LeExp-1-1.4 and was sequenced in entirety on both strands. LeExp-1-1.4 consists of 581 bp of the 5' region upstream of the LeExp-1 cDNA, 504 bp of exon 1, followed by a 343 bp intron, and 76 bp of the second exon. The regions of LeExp-1-1.4 that overlap the LeExp-1 cDNA are 99.9% identical to the published cDNA sequence (Rose, 1997) indicating that this region is the promoter for the LeExp-1 gene.

Other objects, advantages, and novel features of the present invention will become apparent from the detailed description that follows, when considered in conjunction with the associated drawings.

BRIEF DESCRIPTION OF THE DRAWINGS

FIG. 1 is a DNA sequence analysis of 581 bp of the LeExp-1 promoter (position 581 is indicated by the "*" in the sequence) and a portion of the first exon of LeExp-1 SEQ ID NO:2. Two potential auxin-regulatory elements (AuxRE), and the potential Sp8a and Sp8b elements, are indicated in bold. Two 10 bp repeats and two 7 bp repeats are underlined. The putative CAAT and TATA boxes in the 5' flanking region are numbered as 1 and 2, respectively. The +1 (↑) denotes the predicted transcriptional start site of the LeExp-1 mRNA. The amino acids of the encoded polypeptide are designated in the single-letter code.

FIG. 2 is the DNA sequence analysis of the 581 bp LeExp-1 promoter and is the basis for SEQ ID NO: 1.

DESCRIPTION OF THE PREFERRED EMBODIMENT

Referring now to FIGS. 1 and 2 and SEQ ID NO: 1, there is shown a preferred embodiment or sequence of the subject invention. For the subject invention, the materials and methods follow immediately below.

Materials and Methods
1. Bacterial Strain and Growth Condition

E. coli XL1-Blue cells (Stragene, Inc) were cultured in Luria-Bertani (LB) medium [1%(w/v) Bacto-tryptone, 1% (w/v) NaCl. 0.5% (w/v) Bacto-yeast extract, pH 7.0] at 37° C. with vigorous shaking. When appropriate, 20 µg/ml kanamycin was added to the LB broth. For plates, the LB medium was solidified by adding 1.5% Bacto-agar (Difco).
2. DNA Manipulations 2-1. Minipreparation of Plasmid DNA Plasmid DNA was isolated using the High Pure Plasmid Isolation Kit (Boehringer Mannheim) for mini preparations according to the manufacturer's standard protocol. Four ml of an overnight culture grown in LB with the appropriate antibiotic was spun for 1 min at 10,000×g. The pelleted bacterial cells were resuspended in 250 µl of resuspension buffer (50 mM Tris-HCl, 10 mM EDTA, pH 8.0, 100 µg/ml RNase A), and mixed well. 250 µl of lysis buffer (0.2 M NaOH, 1% SDS) was added, mixed gently and incubated for 5 min at room temperature. Following this, 350 µl of chilled binding buffer (4 M guanidine hydrochloride, 0.5M potassium acetate, pH 4.2) was added and mixed by inverting 3 to 6 times. After incubation on ice for 5 min, the sample was centrifuged for 10 min at 13,000×g. The supernatant was collected and applied to the High Pure filter tube. The filter tube was combined with the collection tube and centrifuged for 30 sec at 13,000×g. The filter tube was then washed with 700 µl of wash buffer II (20 mM NaCl, 2 mM Tris-HCl, pH 7.5, 80% (v/v) ethanol) and spun for 30 sec at 13,000×g. The flow-through was discarded and the filter tube spun for an additional 30 sec. The High Pure filter tube was placed in an autoclaved 1.5 ml microcentrifuge tube, and the plasmid DNA was eluted by adding 100 µl ddH$_2$O followed by centrifugation at 13,000×g for 30 sec.

2-2. Preparation of Tomato Genomic DNA

Genomic DNA was extracted from young leaves of tomato *Lycopersicon esculentum* following the procedure of Stewart and Via (1993) with slight modification. Young tomato leaf (1 g) was pulverized in liquid nitrogen in a mortar. 10 ml of C-TAB extraction buffer [2% hexadecyltrimethyl-ammonium bromide (C-TAB), 1.42 M NaCl, 20 mM EDTA, 100 mM Tris Cl pH 8.0, 2% Polyvinylpyrolidone (PVP), 5 mM ascorbic acid, 0.5% β-mercaptoethanol 100 µg/ml RNase A] was added, and the tissue was ground to give a slurry. This was incubated at 60° C. for 1 h and then centrifuged at 12,000×g for 10 min. The supernatant was collected and 10 ml of phenol: chloroform: isoamyl alcohol (25:24:1) was added. This was mixed to yield an emulsion and centrifuged at 12,000×g at 4° C. for 10 min. The aqueous phase was collected and combined with an equal volume of 100% isopropanol. The solution was mixed by vortexing and recentrifuged at 16,000 rpm at 4° C. for 20 min. The supernatant was discarded and the precipitate was washed in 10 ml of 70% ethanol at −20° C. overnight. The precipitate was recollected by centrifugation, air-dried, and dissolved in 200 µl of TE buffer (10 mM Tris-HCl pH 8.0, 1 mM EDTA pH 8.0) The genomic DNA was used for isolation of the gene encoding LeExp-1 by PCR as described below.

3. Isolation of the Gene Encoding LeExp-1 and its Promoter 3-1. Inverse PCR

The following inverse PCR was performed according to Ochman et al (1993), with slight modification. A pair of oligonucleotide primers was designed based on the published sequence of the LeExp-1 cDNA (Rose et al, 1997; Genbank accession number U82123) in such a way that they annealed to the target DNA template 29 bp apart with their 3'-termini oriented in opposite directions.

The oligonucleotide primers were designated LeExp-1-7 (5' GGAACAATGGGCGGTGCG TGTGG 3') SEQ ID NO:3 and LeExp-1-8 rev. (5' GCATGTGCAGTTTCCCAT-GAACCACC 3'), SEQ ID NO:4 corresponding to the nucleotide sequence 169–191 and 140–115 of the LeExp-1 cDNA, respectively. Two nested primers were also designed and designated LeExp-1-2 and LeExp-1-3 rev. The sequence of each follows with the position of each on the LeExp-1 cDNA shown in parentheses: LeExp-1-2, 5' TTATA-CAGCCA AGGATACGG 3'(201–221) SEQ ID NO:5 and LeExp-1-3 rev, 5' GTAAACACCAGGGATTCTTCC 3'(111-91) SEQ ID NO:6.

Genomic DNAs were isolated from the young leaves of tomato, *Lycopersicon esculentum*, as described above. The genomic DNAs were treated with one restriction enzyme, BamHI, BgLII, or BcLI, or a two enzyme combination of BamHI, BgLII, or BcLI in a volume of 20 µl consisting of 2 µg of DNA, 1× restriction enzyme buffer, and 20 units of restriction enzyme(s) at 30° C. (BcLI) and 37° C. (BamHI, and BgLII) for 3 hr. The digested DNAs were purified using the High Pure PCR Purification Kit (Boehringer Mannheim) according to the manufacturers instructions and eluted in 100 µl of distilled water.

Ligations were set up in 100 µl of ligation buffer containing 66 mM Tris-HCl, 5 mM MgCl$_2$, 1 mM dithioerythritol, 1 mM ATP, and 1 unit T4 DNA ligase (Boehringer Mannheim) at three DNA concentrations (500, 200 or 20 ng per reaction). Reactions were incubated at 16° C. for 16 hr, followed by heat inactivation at 65° C. for 15 min, and repurified by High Pure PCR Purification Kit (Boehringer Mannheim).

Inverse PCR was carried out in 50 µl of 1× Expand HF buffer containing 2.5 mM $MgCl_2$, 0.2 mM of each dNTP, 40 pmol of each primer and 40 µl of purified ligation products (corresponding to approximately 160 ng, 32 ng and 6.4 ng of template DNA). After a preheating step at 95° C. for 10 min 2.6 units of Expand™ DNA polymerase (Boehringer Mannheim) was added and inverse PCR reactions were performed in a PTC-1000 Programmable thermal controller manufactured by MJ Research, Inc. (Watertown, Mass.) with amplification for 38 cycles subdivided into 5 different segments as follows. Segment 1:1 cycle (9° C., 2 min), segment 2:10 cycles (94° C., 15 sec; 57° C., 30 sec; 68° C., 5 min), segment 3:11 cycles (94° C., 15 sec; 57° C., 30 sec; 68° C., 6 min), segment 4:12 cycles (94° C., 15 sec; 57° C., 30 sec; 68° C. 7 min), and segment 5:1 cycle (72° C., 5 min).

The second amplification was set up with the two nested primers, LeExp-1-2 and LeExp-1-3 rev., in a 50 µl volume reaction including 1× reaction buffer (10 mM Tris-HCl, pH 9.0, 50 mM KCl 0.1% Triton X-100, 1.5 mM $MgCl_2$) 0.125 mM of each dNTP, 40 pmol of each primer, 1 µl of the first PCR reaction, 1 unit of Taq polymerase (Promega), and deionized distilled H2O. The amplification was carried out for 30 cycles each consisting of denaturation at 94° C. for 2 min, primer annealing at 55° C. for 30 sec, and primer extension at 72° C. for 3 min.

After the cycles were completed, 10 µl of the mixture was electrophoresed on a 0.7% agarose gel containing 1 µg/ml ethidium bromide along with 1 kb and 100 bp DNA ladders (New England BioLabs) as molecular weight markers. Following electrophoresis, the gel was observed on an UV transilluminator, and its image recorded using a Polaroid camera. The amplified PCR products were gel-purified and recovered with High Pure PCR Product Purification Kit (Boehringer Mannheim)

The purified 1.4 kb DNA fragment was then inserted into pCR1000 vector (InVitrogen). Ligation reactions in a final volume of 10 µl consisted of 25 ng of the purified PCR products, 1× ligation buffer (30 mM Tris-HCl, pH 7.8, 10 mM $MgCl_2$, 10 mM DTT, 1 mM ATP), 20 ng of pCR1000 vector, and deionized distilled water. The reaction was initiated by addition of 3 Weiss units of T4 DNA Ligase (Promega) and incubated overnight at 16° C. The ligated plasmids were transformed into competent XL1-Blue cells using the method described below in the section 3-2 Transformation of *E. coli*.

3-2. Transformation of *E. coli*

Preparation of competent *E. Coli* XL1-Bule cells (Stratagene, Inc) and transformation were based on Hanahan's method (1983) as described by Sambrook et al.,(1989).

To prepare frozen stock of competent cells, FSB buffer (10 mM potassium acetate, pH 7.5, 45 mM $MnCl_2.4H_2O$, 10 mM $CaCl_2.2H_2O$, 100 mM KCl, 3 mM hexamminecobalt chloride and 10% glycerol) and dimethyl sulfoxide (DMSO) were used as recommended in the above protocol.

For a color selection of recombinants, the transformed *E. coli* XL1-Blue cells were plated onto Luria-Bertani (LB) plate (1% Bacto-tryptone, 1% NaCl. 0.5% Bacto-yeast extract, 1.5% Bacto-agar, pH 7.0) containing, 20 µg/ml kanamycin, 40 µl/plate of a stock solution of X-gal (20 mg/ml in dimethylformamide), and 4 µl/plate of a solution of isopropylthio-β-D-galactoside (IPTG) (200 mg/ml). The plates were incubated overnight at 37° C. The white colonies containing recombinant plasmid DNA were selected.

3-3. DNA Sequencing

For DNA sequencing, plasmid DNA consisting of the 1.4 kb LeExp-1 fragment which includes 581 bp of the LeExp-1 promoter inserted into pCR1000 was isolated using the High Pure Plasmid Isolation Kit as described above and sent to the Microchemical Core Facility, San Diego State University, San Diego, Calif. or to Davis Sequencing, Davis, Calif. DNA sequencing reactions were primed with standard oligonucleotide primers supplied by the sequencing facilities and with gene specific primers designed based on the sequences obtained from initial DNA sequencing runs and synthesized by Operon Technologies, Inc.(Alameda, Calif.). Both strands were sequenced in entirety. Individual DNA sequences were assembled with the software MacDNasis 2.0 (Hitachi Software Engineering, Co).

The conclusion that the subject promoter is a strong fruit-specific promoter is based on the results obtained by Rose et al. (1997) and Brummel et al. (1999) that show that the LeExp-1 mRNA accumulates to a high level specifically in tomato fruit.

REFERENCES

Brummell D. A, Harpster M H, Dunsmuir P (1999) Differential expression of expansin gene family members during growth and ripening of tomato fruit. Plant Mol Biol. 39(1):161–9

Ochman, H., Ayala, F. J., Hartl, D. L. (1993) Use of polymerase chain reaction to amplify segments outside boundaries of known sequences. Methods in Enzymology 218: 309–332.

Rose J K C, Lee H H, Bennett A B (1997) Expression of a divergent expansin gene is fruit-specific and ripening-regulated. Proc Natl Acad Sci U S A. 94(11):5955–60

Stewart, C. N. and Via, L. E. (1993). A rapid C-TAB DNA isolation technique useful for RAPD fingerprinting and other PCR amplification. Biotechniques 14 (5):748–749.

Although the foregoing invention has been described in some detail by way of illustration and example for purposes of clarity of understanding, it will be obvious that certain changes and modifications may be practiced by those skilled in the art and be within the realm of the subject disclosure.

What is claimed is:

1. An isolated promoter sequence shown in SEQ ID NO: 1.

* * * * *

UNITED STATES PATENT AND TRADEMARK OFFICE
CERTIFICATE OF CORRECTION

PATENT NO. : 6,340,748 B1
DATED : January 22, 2002
INVENTOR(S) : Ro et al.

It is certified that error appears in the above-identified patent and that said Letters Patent is hereby corrected as shown below:

Title page,
Item [*], Notice, delete the phrase "by 0 days" and insert -- by 12 days --

Signed and Sealed this

Twenty-first Day of September, 2004

JON W. DUDAS
*Director of the United States Patent and Trademark Office*